(12) United States Patent
Brunner et al.

(10) Patent No.: US 10,155,083 B2
(45) Date of Patent: Dec. 18, 2018

(54) APHERESIS BOWL WITH IMPROVED VIBRATION CHARACTERISTICS

(71) Applicant: Haemonetics Corporation, Braintree, MA (US)

(72) Inventors: Bruce Brunner, Bridgewater, MA (US); Christopher J. Caputo, Raynham, MA (US)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 15/594,933

(22) Filed: May 15, 2017

(65) Prior Publication Data
US 2017/0246377 A1 Aug. 31, 2017

Related U.S. Application Data

(60) Division of application No. 13/898,743, filed on May 21, 2013, now Pat. No. 9,682,185, which is a
(Continued)

(51) Int. Cl.
*A61M 1/36* (2006.01)
*B04B 5/04* (2006.01)
*B04B 7/08* (2006.01)

(52) U.S. Cl.
CPC ........ *A61M 1/3693* (2013.01); *A61M 1/3696* (2014.02); *B04B 5/0442* (2013.01);
(Continued)

(58) Field of Classification Search
CPC .............. A61M 1/3693; A61M 1/3696; A61M 2205/42; B04B 5/0442; B04B 7/08; B04B 2005/0464
See application file for complete search history.

(56) References Cited

U.S. PATENT DOCUMENTS 447,530 A 3/1891 Wahlin
528,683 A 11/1894 Ohlsson
(Continued)

FOREIGN PATENT DOCUMENTS

CN 2404592 11/2000
CN 2492231 5/2001
(Continued)

OTHER PUBLICATIONS

Machine translation of JP-2006247217-A (Year: 2006).*
(Continued)

*Primary Examiner* — Timothy C Cleveland
(74) *Attorney, Agent, or Firm* — Sunstein Kann Murphy & Timbers LLP

(57) ABSTRACT

A centrifuge bowl for separating whole blood into blood components includes a rotatable body, and inlet, and a plurality of vibration reduction members. The rotatable body has a body portion and a neck portion. The body portion defines an interior for receiving whole blood, and the body is rotatable to separate the whole blood into a plurality of blood components. The inlet is in fluid communication with the interior of the rotatable body, and is configured to introduce the whole blood into the rotatable body. The plurality of vibration reduction members are spaced about the neck portion, and are configured to reduce vibration of the centrifuge bowl as the bowl is rotated.

20 Claims, 9 Drawing Sheets

Related U.S. Application Data continuation of application No. PCT/US2010/057820, filed on Nov. 23, 2010.

(52) U.S. Cl.
CPC ........... *B04B 7/08* (2013.01); *A61M 2205/42* (2013.01); *B04B 2005/0464* (2013.01)

(56) References Cited

U.S. PATENT DOCUMENTS

| | | | |
|---|---|---|---|
| 754,909 | A | 3/1904 | Springer |
| 764,489 | A | 7/1904 | McLeod |
| 825,721 | A | 7/1906 | Hartmann |
| 886,393 | A | 5/1908 | Morgan |
| 1,603,726 | A | 10/1926 | Thomsen |
| 3,125,516 | A | 3/1964 | Kaldewey |
| 3,675,846 | A | 7/1972 | Drucker |
| 3,771,353 | A | 11/1973 | Jenkins |
| 3,899,128 | A | 8/1975 | Joyce |
| 4,059,108 | A | 11/1977 | Latham, Jr. |
| 4,086,924 | A | 5/1978 | Latham, Jr. |
| 4,140,268 | A | 2/1979 | Lacour |
| 4,152,270 | A | 5/1979 | Cornell |
| 4,204,537 | A | 5/1980 | Latham, Jr. |
| 4,300,717 | A | 11/1981 | Latham, Jr. |
| 4,718,888 | A | 1/1988 | Darnell |
| 4,943,273 | A | 7/1990 | Pages |
| 4,983,158 | A | 1/1991 | Headley |
| 5,387,174 | A | 2/1995 | Rochat |
| 9,682,185 | B2 | 6/2017 | Brunner et al. |
| 2008/0290752 | A1 | 11/2008 | Yamamoto et al. |
| 2009/0060251 | A1 | 3/2009 | Maeda |
| 2009/0129976 | A1 | 5/2009 | Hoshino et al. |
| 2010/0167388 | A1 | 7/2010 | Kessler |
| 2010/0311559 | A1* | 12/2010 | Miltenyi ............ A61M 1/3693 494/10 |

FOREIGN PATENT DOCUMENTS

| | | | |
|---|---|---|---|
| CN | 101124862 | | 2/2008 |
| CN | 101237173 | | 8/2008 |
| CN | 101242864 | | 8/2008 |
| CN | 101378603 | | 3/2009 |
| JP | 55-500526 | | 8/1980 |
| JP | 09-192215 | | 7/1997 |
| JP | 2001-508179 | | 6/2001 |
| JP | 2006-034532 | | 2/2006 |
| JP | 2006247217 | A * | 9/2006 ........... B04B 5/0442 |
| RU | 31964 | | 9/2003 |
| TW | 238548 | | 1/1995 |
| WO | WO 80/00227 | | 2/1980 |
| WO | WO 98/30887 | | 7/1998 |
| WO | WO 2007/053139 | | 5/2007 |
| WO | WO 2009/072006 | | 6/2009 |

OTHER PUBLICATIONS

Qu, et al., "Vibration during the cutting process," *Instrument Manufacturing Technologies*, pp. 70-71, Jan. 2005.
Qu, et al., "Vibration during the cutting process," *Instrument Manufacturing Technologies*, pp. 70-71, Jan. 2005 [English Translation].
Russian Patent Office, Official Action—Application No. 2013128603/05, dated Oct. 13, 2014, 5 pages.
Russian Patent Office, Office Action—Application No. 2013128603/05, dated Oct. 13, 2014, 4 pages. [English Translation].
Jørgen Olsen, Authorized officer Danish Patent and Trademark Office, Singapore Search Report and Written Report—Application No. 2013039268, dated Aug. 15, 2014, 17 pages.
Jørgen Olsen, Authorized officer Intellectual Property Office of Singapore, Examination Report—Application No. 2013039268, dated Apr. 7, 2015, 10 pages.
Josef Leitner, Authorized officer European Patent Office, International Search Report—Application No. PCT/US2010/057820, dated Jul. 26, 2011, 4 pages.
European Patent Office, Examination Report—Application No. 10 787 220.2, dated Oct. 30, 2015, 6 pages.
European Patent Office, Examination Report—Application No. 10 787 220.2, dated Jul. 1, 2016, 4 pages.
Korean Patent Office, Preliminary Rejection—Application No. 10-2013-7013724, dated Jul. 14, 2016, 10 pages.
Korean Patent Office, Notice of Preliminary Rejection—Application No. 10-2013-7013724, dated Jul. 14, 2016, 9 pages. [English Translation].
State IP Property Office of the People's Republic of China, Office Action—Application No. 201080071064.0, dated Mar. 25, 2014, 9 pages.
State IP Property Office of the People's Republic of China, Notification of the First Office Action—Application No. 201080071064.0, dated Mar. 25, 2014, 9 pages. [English Translation].
State IP Property Office of the People's Republic of China, Second Office Action—Application No. 201080071064.0, dated Dec. 12, 2014, 6 pages.
State IP Property Office of the People's Republic of China, Notification of the Second Office Action—Application No. 201080071064.0, dated Dec. 12, 2014, 7 pages. [English Translation].
State IP Property Office of the People's Republic of China, Third Office Action—Application No. 201080071064.0, dated Jun. 5, 2015, 11 pages.
State IP Property Office of the People's Republic of China, Notification of the Third Office Action—Application No. 201080071064.0, dated Jun. 5, 2015, 7 pages. [English Translation].
State IP Property Office of the People's Republic of China, First Office Action—Application No. 201610195897.7, dated Jul. 3, 2017, 7 pages.
State IP Property Office of the People's Republic of China, First Office Action—Application No. 201610195897.7, dated Jul. 3, 2017, 8 pages. [English Translation].
Nora Lindner, Authorized Officer The International Bureau of WIPO, International Preliminary Report on Patentability—Application No. PCT/US2010/057820, dated May 28, 2013, 7 pages.
Taiwan Intellectual Patent Office, Office Action and Search Report—Application No. 100142717, dated Sep. 7, 2015, 9 pages.
Taiwan Intellectual Patent Office, Office Action and Search Report—Application No. 100142717, dated Sep. 7, 2015, 1 page. [English Translation].
Takahiro Okita, Authorized officer Japanese Patent Office, Office Action—Application No. 2012-545977, dated Apr. 23, 2013, 2 pages.
Takahiro Okita, Authorized officer Japanese Patent Office, Official Action (Notification of Reason for Rejection)—Application No. 2012-545977, dated Apr. 23, 2013, 3 pages [English Translation].
Takahiro Okita, Authorized officer Japanese Patent Office, Official Action—Application No. 2012-545977, dated Oct. 17, 2013, 2 pages.
Takahiro Okita, Authorized officer Japanese Patent Office, Final Decision for Rejection—Application No. 2012-545977, dated Oct. 17, 2013, 2 pages. [English Translation].
Third Patent Examination Dept. Japanese Patent Office, Office Action—Application No. 2014-32806, dated Apr. 16, 2015, 4 pages.
Third Patent Examination Dept. Japanese Patent Office, Notification of Reasons for Rejection—Application No. 2014-32806, dated Apr. 16, 2015, 4 pages. [English Translation].
This application relies, under 35 U.S.C. § 120, on the earlier filing date of prior U.S. Appl. No. 13/898,743, filed May 21, 2013.

* cited by examiner

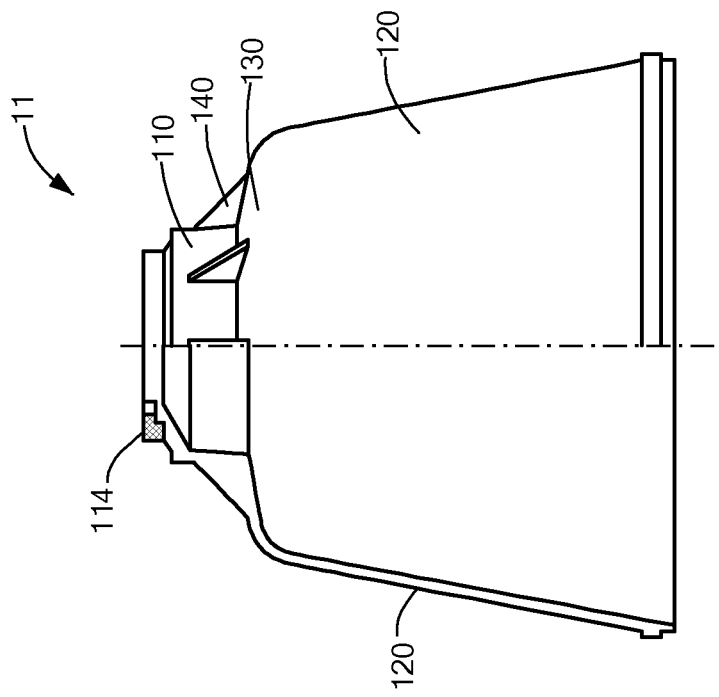
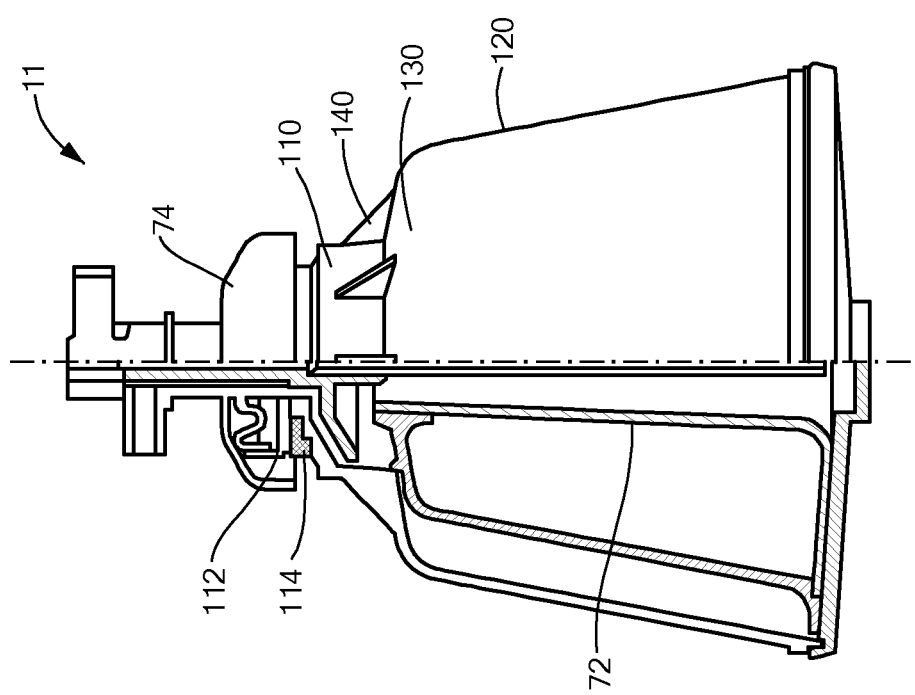
FIG. 4B
FIG. 4A

APHERESIS BOWL WITH IMPROVED VIBRATION CHARACTERISTICS

PRIORITY

This application is a divisional of co-pending U.S. patent application Ser. No. 13/898,743, entitled "Apheresis Bowl with Improved Vibration Characteristics," filed May 21, 2013, and naming Bruce Brunner and Christopher J. Caputo as inventors, the disclosure of which is incorporated herein, in its entirety, by reference.

U.S. application Ser. No. 13/898,743, in turn, is a continuation of Patent Cooperation Treaty application PCT/US2010/057820, entitled "Apheresis Bowl with Improved Vibration Characteristics," filed Nov. 23, 2010, and naming Bruce Brunner and Christopher J. Caputo as inventors, the disclosure of which is incorporated herein, in its entirety, by reference.

TECHNICAL FIELD

The present invention relates to systems and method for blood apheresis, and more particularly to reducing vibration and noise within blood component separation devices.

BACKGROUND ART

Apheresis is a procedure in which individual blood components can be separated and collected from whole blood temporarily withdrawn from a subject. Typically, whole blood is withdrawn through a needle inserted into a vein of the subjects arm and into a cell separator, such as a centrifugal bowl. Once the whole blood is separated into its various components, one or more of the components can be removed from the centrifugal bowl. The remaining components can be returned to the subject along with optional compensation fluid to make up for the volume of the removed component. The process of drawing and returning continues until the quantity of the desired component has been collected, at which point the process is stopped. A central feature of apheresis systems is that the processed but unwanted components are returned to the donor. Separated blood components may include, for example, a high density component such as red blood cells, an intermediate density component such as platelets or white blood cells, and a lower density component such as plasma

SUMMARY OF THE INVENTION

In accordance with some embodiments of the present invention, a centrifuge bowl for separating whole blood into blood components includes a rotatable body, an inlet, and a plurality of vibration reduction members. The rotatable body may include a body portion and a neck portion. The body portion defines an interior for receiving whole blood and is rotatable to separate the whole blood into a plurality of blood components. The inlet may be in fluid communication with the interior of the rotatable body, and configured to introduce the whole blood into the rotatable body. The plurality of vibration reduction members may be spaced (e.g., radially) about the neck portion, and may reduce vibration of the centrifuge bowl as the bowl is rotated. The vibration reduction members may be rib members and may be curved or straight.

The centrifuge bowl may also include an outlet that is in fluid communication with the interior of the bowl. The outlet may be used to remove one or more of the blood components from the centrifuge bowl. In order to allow the centrifuge bowl to rotate and maintain a seal, the centrifuge bowl may also have a rotary seal attached to the rotatable body, and coupling the inlet to the body portion. The centrifuge bowl may also include a core that is coaxial with the interior. The core creates a whole blood separation region between the outer wall of the core and the inner wall of the rotatable body.

In accordance with further embodiments, the centrifuge bowl may include a shoulder portion extending between the neck portion and the body portion. In such embodiments, the vibration reduction member(s) may be a thickened area on the shoulder portion. The thickened area may increase in thickness towards the axis of rotation of the bowl. The increase in thickness may be stepped.

In accordance with additional embodiments, a blood processing system for separating whole blood into blood components may include a venous access device for drawing whole blood from a subject, a blood component separation device, means for extracting one or more blood components from the separation device, at least one storage container for storing the at least one blood component extracted from the blood component separation device, and means for returning remaining blood components to the subject. The blood component separation device separates the whole blood into the plurality of components, and may include a centrifuge bowl.

The centrifuge bowl may have a body portion and a neck portion. The body portion defines an interior for receiving the whole blood, and is rotatable to separate the whole blood into the plurality of blood components. The neck portion has a plurality of vibration reduction members that reduce vibration of the centrifuge bowl as the bowl is rotated. The plurality of vibration reduction members may be radially spaced about the neck portion and may be straight and/or curved ribs members. The blood component separation device may also include (1) an outlet that is in fluid communication with the interior of the bowl and configured to remove one or more of the blood components from the centrifuge bowl, (2) a rotary seal attached to the rotatable body and fluidly coupling the inlet to the body portion, and/or (3) a core that is coaxial with the interior and creates a whole blood separation region between the outer wall of the core and the inner wall of the rotatable body.

Additionally or alternatively, the vibration reduction members may be thickened areas on a shoulder portion that extends between the neck portion and the body portion. The thickened area(s) may increase in thickness and may be stepped. The centrifuge bowl may also have an inlet in fluid communication with the interior.

In accordance with additional embodiments, a centrifuge bowl for separating whole blood into blood components may include a rotatable body, an inlet, and at least one vibration reduction member. The rotatable body may have a body portion, a shoulder portion, and a neck portion. The body portion may define an interior for receiving whole blood, and may be rotatable to separate the whole blood into a plurality of blood components. The shoulder portion may extend between the body portion and the neck portion.

The inlet may be in fluid communication with the interior of the rotatable body, and may be configured to introduce the whole blood into the rotatable body. The at least one vibration reduction member may be located on the shoulder portion and may be configured to stiffen at least a portion of the rotatable body and reduce vibration of the centrifuge bowl as the bowl is rotated. The at least one vibration reduction member may include a plurality of rib members (e.g., curved rib members or straight rib members). Additionally or alternatively, the at least one vibration reduction member may include a thickened are located on the shoulder portion. The thickened area may increase in thickness towards an axis of rotation of the bowl. The increase in thickness may be stepped.

BRIEF DESCRIPTION OF THE DRAWINGS

The foregoing features of the invention will be more readily understood by reference to the following detailed description, taken with reference to the accompanying drawings, in which:

FIG. 4A schematically shows a side view of a centrifuge bowl with a portion in cross-section and having vibration reduction members, in accordance with embodiments of the present invention;

FIG. 4B schematically shows a side view of a centrifuge bowl without a rotart seal and having vibration reduction members, in accordance with embodiments of the present invention;

DETAILED DESCRIPTION OF SPECIFIC EMBODIMENTS

Illustrative embodiments of the present invention provide a system, and blood component separation device for performing a blood apheresis procedure. Additionally, various embodiments of the present invention reduce the vibration and noise seen in some prior art separation devices. For example, embodiments of the present invention may include one or more vibration reduction members. Details of illustrative embodiments are discussed below.

Figure 1:
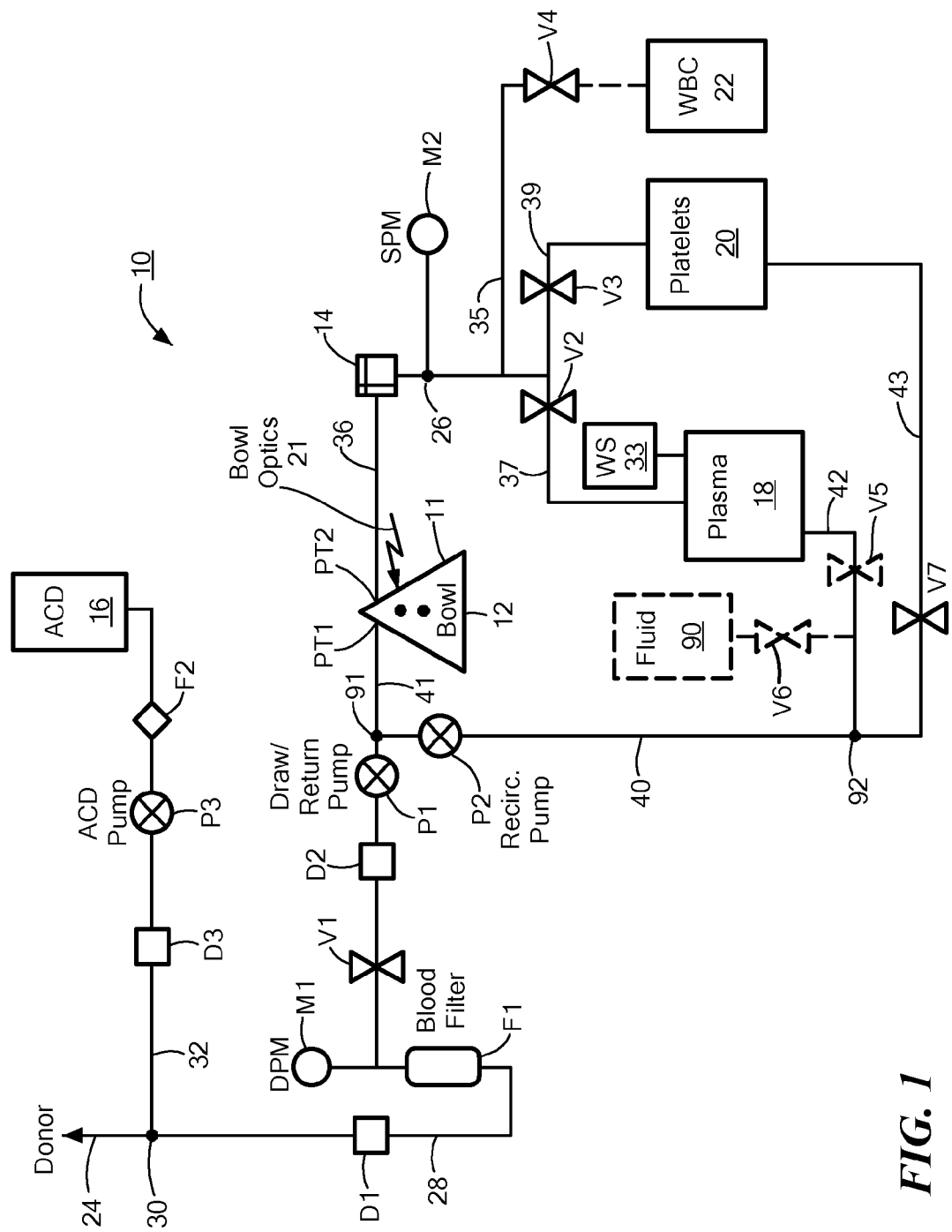
FIG. 1 shows a schematic diagram of an apheresis system in accordance with embodiments of the present invention.
Figure 2:
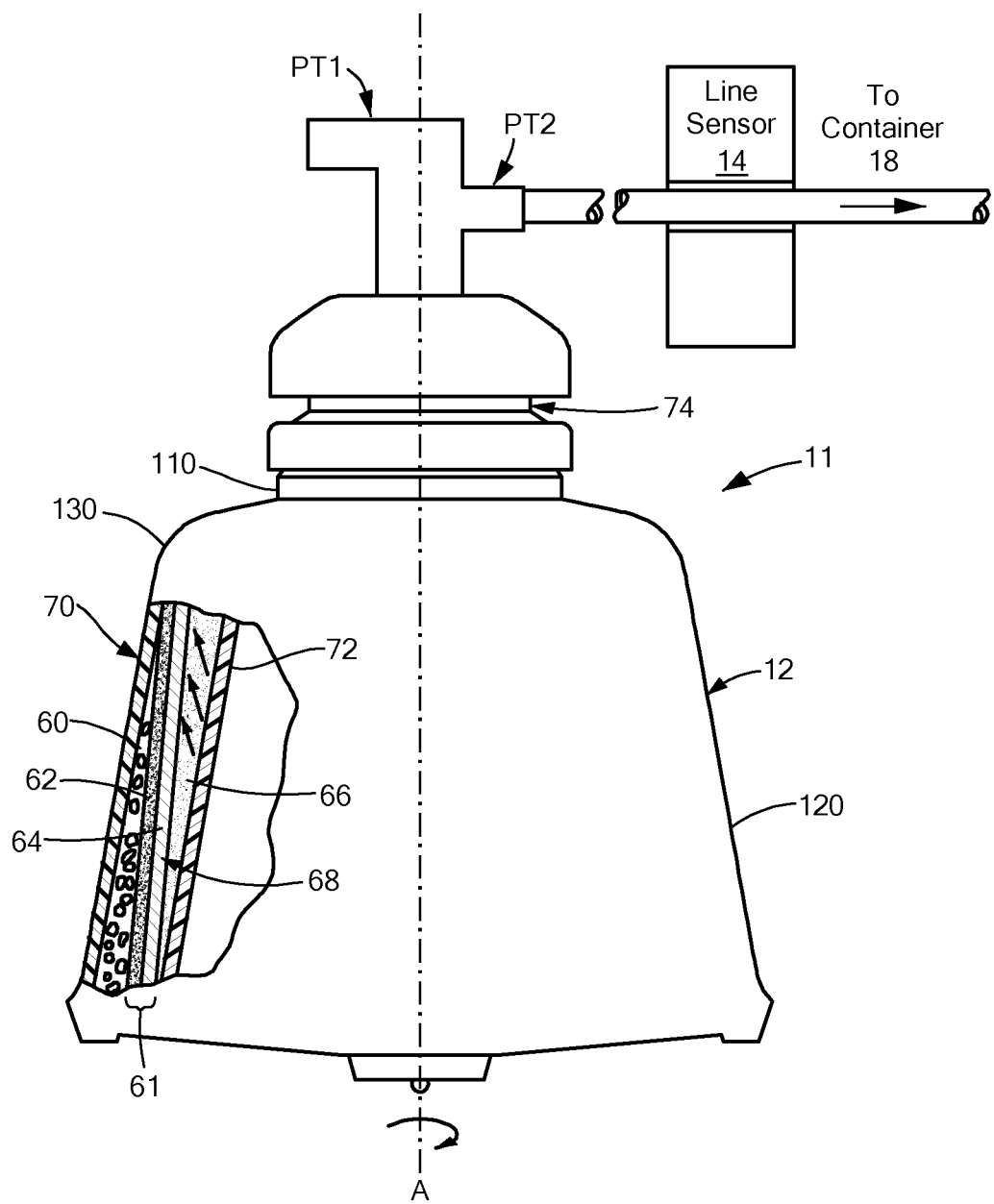
FIG. 2 schematically shows a side view of a blood component separate device for use with the apheresis system of FIG. 1, in accordance with embodiments of the present invention.

As shown in FIGS. 1 and 2, and as mentioned above, an apheresis system 10, in accordance with embodiments of the present invention, withdraws whole blood from a subject through a venous access device 24 using a withdraw pump P1. The venous access device 24 can be any number of devices capable of accessing a subject's veins including, but not limited to a phlebotomy needle. As the system 10 withdraws the whole blood from the subject, the blood passes through a draw/return line 28 and enters a blood component separation device 11, such as a Latham type centrifuge. The blood component separation device 11 separates the whole blood into its constituent components (e.g., red blood cells, white blood cell, plasma, and platelets). Although a Latham type centrifuge is mentioned above, other types of separation chambers and devices may be used, such as, without limitation, an integral blow-molded centrifuge bowl, as described in U.S. Pat. Nos. 4,983,156 and 4,943,273, which are hereby incorporated by reference.

As the system 10 withdraws the whole blood from the subject, the system 10 may introduce anticoagulant into the withdrawn whole blood to prevent the blood from coagulating within the lines or within the blood component separation device 11. To that end, the system 10 may include an anticoagulant line 32 fluidly connected to an anticoagulant source 16 (e.g., a bag of anticoagulant) at one end, and the venous-access device 24 (or the draw/return line 28 via a y-connector 30) at the other end. An anti-coagulant pump P3, through which the anticoagulant line 32 passes, may control the flow of anticoagulant within the anti-coagulant line 32 and the amount of anticoagulant introduced into the whole blood. Although the anticoagulant can be added to the whole blood at any point, it is preferred that the anticoagulant be introduced as close as possible to the venous-access device 24.

The anticoagulant line 32 may also include a bacteria filter F2 that prevents any bacteria in the anticoagulant source 16, the anticoagulant, or the anticoagulant line 32 from entering the system 10 and/or the subject. Additionally, the anticoagulant line 32 may include an air detector D3 that detects the presence of air within the anticoagulant. The presence of air bubbles within any of the system 10 lines can be problematic for the operation the system 10 and may also be harmful to the subject if the air bubbles enter the blood stream. Therefore, the air detector D3 may be connected to an interlock that stops the flow within the anticoagulant line 32 in the event that an air bubble is detected (e.g., by stopping the anticoagulant pump P3 or closing a valve on the anticoagulant line 32), thereby preventing the air bubbles from entering the subject.

Once a desired amount of anti-coagulated whole blood is withdrawn from the subject and contained within the blood component separation device 11, the blood component separation device 11 separates the whole blood into several blood components. For example, the blood component separation device 11 may separate the whole blood into a first, second, third, and, perhaps, fourth blood component. More specifically, the blood component separation device 150 can separate the whole blood into plasma, platelets, red blood cells, and, perhaps, white blood cells.

As shown in FIG. 2, when a Latham centrifuge is used, the blood component separation device 11 includes a rotatable bowl 12 and stationary input and output ports PT1 and PT2 fluidly coupled to the bowl interior by a rotary seal 74. The rotatable bowl may include a neck portion 110 coupled to the rotary seal 74, and a body portion 120 that defines the interior volume of the separation device (e.g, the interior volume of the rotatable bowl 12). The bowl 12 (e.g., the body portion 120) may have a frustoconical shape. The rotatable bowl 12 may also include a shoulder portion 130 extending between and connecting the neck portion 110 and the body portion 120.

Additionally, some embodiments may have a core 72 that occupies a volume coaxial with the interior of bowl 12 and provides a separation region between the wall of the core 72 and the outer bowl wall 70. The draw/return line 28 fluidly connects the venous access devices 24 (e.g., the phlebotomy needle) and the input port PT1. In some embodiments, the venous access device 24 may be replaced with a whole blood bag (not shown) in case the whole blood is to be first pooled and then supplied. In such embodiments, the draw line 28 will fluidly connect the whole blood bag with the input port PT1.

As mentioned above, the blood component separation device 11 separates the whole blood into its constituent components. In particular, as the bowl 12 rotates, centrifugal forces separate the anticoagulated whole blood admitted into the bottom of the bowl into red blood cells (RBC), white blood cells (WBC), platelets and plasma. The number of rotations of the bowl 12 can be selected, for example, within a range of 4,000 to 6,000 rpm, and is typically 4,800 rpm. The blood is separated into different fractions in accordance with the component densities. The higher density component, i.e., RBC 60, is forced to the outer wall 70 of the bowl 12 while the lower density plasma 66 lies nearer the core 72. A buffy coat 61 is formed between the plasma 66 and the RBC 60. The buffy coat 61 is made up of an inner layer of platelets 64, a transitional layer 68 of platelets and WBC and an outer layer of WBC 62. The plasma 66 is the component closest to the outlet port from the separation region and is the first fluid component displaced from the bowl 12 via the outlet port PT2 as additional anticoagulated whole blood enters the bowl 12 through the inlet port PT1.

The system 10 may also include an optical sensor 21 that may be applied to a shoulder portion of the bowl 12. The optical sensor 21 monitors each layer of the blood components as they gradually and coaxially advance toward the core 72 from the outer wall 70 of the bowl 12. The optical sensor 21 may be mounted in a position at which it can detect the buffy coat reaching a particular radius, and the steps of drawing the whole blood from the subject/donor and introducing the whole blood into the bowl 12 may be terminated in response to the detection.

Once the blood component separation device 11 has separated the blood into the various components, one or more of the components can be removed from the blood component separation device 11. For instance, the plasma may be removed to a plasma bag 18 through line 37 (FIG. 1) or a waste bag (not shown). Alternatively, the plasma may be removed to a plasma reservoir (not shown) located on the draw/return line 28, or the white blood cells (WBC) may be removed to one or more white blood cell bags 22 via line 35. Some embodiments of the system 10 may include a weight sensor 33 that measures the amount plasma collected. Although not shown, the platelet bag 20 and the white blood cell bag 22 may include similar weight sensors. The removed plasma may be later reintroduced into the blood component separation device 11 via line 40 and recirculation pump P2 at an increasing rate to extract and send the platelets to a platelet bag 20 via line 39. This process is known as surge elutriation.

In some embodiments, the system 10 may also include a line sensor 14 that can determine the type of fluid (e.g., plasma, platelets, red blood cells etc.) exiting the blood component separation device. In particular, the line sensor 14 consists of an LED which emits light through the blood components leaving the bowl 12 and a photo detector which receives the light after it passes through the components. The amount of light received by the photo detector is correlated to the density of the fluid passing through the line. For example, if plasma is exiting the bowl 12, the line sensor 14 will be able to detect when the plasma exiting the bowl 12 becomes cloudy with platelets (e.g., the fluid existing the bowl 12 is changing from plasma to platelets). The system 10 may then use this information to either stop the removal of blood components from the bowl 12 or redirect the flow by, for example, closing valve V2 and opening valve V3.

Once the system removes the desired components from the blood component separation device 11, the system 10 can return the remaining components to the subject. The system may use the draw/return pump P1 to return the components to the subject via the draw/return line 28, which, as mentioned above, fluidly connects the blood component separation device 11 and the venous-access device 24. Alternatively, if the system 11 is so equipped, the system may return the components to the subject via a dedicated return line. Like the anticoagulant line 32 and the draw/return line 28, the dedicated return line may also have a dedicated return pump that controls the direction, rate, and duration of the fluid flow within the return line. In such embodiments, the return line also fluidly connects to the venous-access device 24, preferably at a point between the return pump and the venous-access device 24. Additionally, in such embodiments, the system 10 will also have a dedicated draw line and draw pump. In some embodiments, the system 10 may include an interlock that stops the withdrawal of whole blood from the subject when the system is returning the first blood component to the subject.

As shown in FIG. 1 and as mentioned briefly above, the system 10 can have a plurality of valves located through-out the system to control the flow of fluid within the system 10. For example, draw/return line 28 may contain a valve V1 that allows flow through the lines when open and prevents flow when closed. Additionally, the lines 35, 37 and 39 leading to the white blood cell, plasma and platelet bags, respectively may have at least one valve V2, V3, V4, and V5 (e.g., line 37 has a valve V2 at the inlet of the plasma bag 18 and a valve V5 at the outlet of the plasma bag 18, and line 39 has a valve V3 at the inlet of the platelet bag 20). Additionally, the inlet to the blood component separation device 11 may have valves (not shown) that either allow or prevent flow to or from the blood component separation device 11. Any of the above mentioned valves can be either manual or automatic. In other words, the valves may be manually operated by the user/technician or can be automatically operated, for example, by a controller, when a particular condition is met (e.g., closing valve V1 when air is detected in the draw/return line 28, as discussed below).

Like the anticoagulant line 32, the draw/return line 28 can also include a number of sensors, filters, and detectors to ensure the safety of the subject and an optimized system operation. In particular, as shown in FIG. 1, the draw/return line 28 may include air detectors D1 and D2 to detect the presence (or absence) of air within the line 28. The air detectors D1 and D2 can be connected to an interlock that, when the detectors D1 and D2 detect air, stops flow within the draw/return line 28 (e.g., by stopping the draw/return pump P1 or closing valve V1). Additionally, the draw line 28 can include a blood filter F1 that removes any bacteria, contamination, or particulates that may be present in the withdrawn blood or the returning components.

Figure 4C:
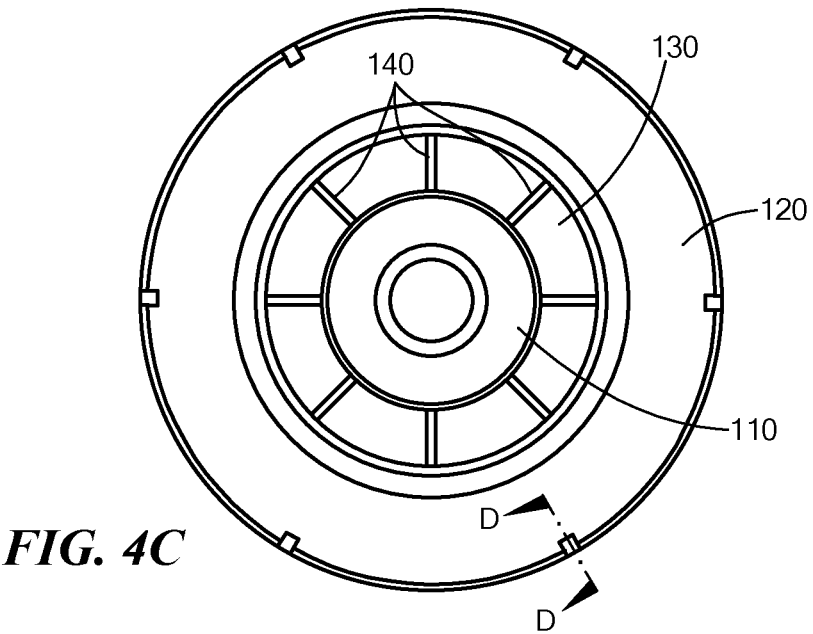
FIG. 4C schematically shows a top view of the centrifuge bowl shown in FIG. 4B, in accordance with embodiments of the present invention.
Figure 4D:
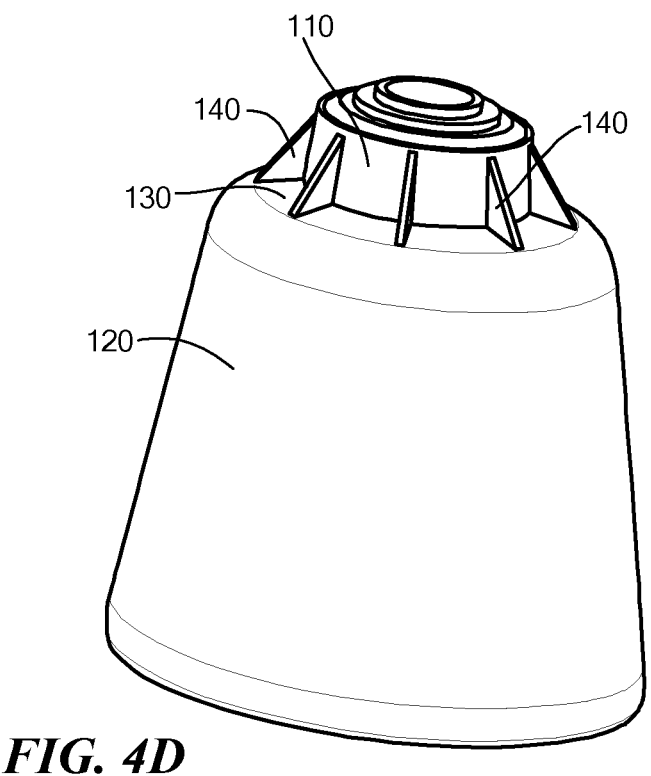
FIG. 4D schematically shows a perspective view of the centrifuge bowl shown in FIG. 4B, in accordance with embodiments of the present invention.

In operation, when the separation device 11/centrifuge bowl 12 is spinning to separate the whole blood into its individual components, various components within the centrifuge bowl 12 may cause the centrifuge bowl 12 to vibrate. For example, the centrifuge bowl may include two or more rings (e.g., a carbon ring 112 and a ceramics ring 114, FIG. 4A) within the neck portion 110 (e.g., within the rotary seal 74) of the bowl 12. As the centrifuge bowl 12 rotates, the friction between the contact surfaces of the rings 112/114 may prevent the rings 112/114 from sliding smoothly against one another. In such cases, the sliding surface of one ring (e.g., the carbon ring 112) may repeatedly stick and slip against the surface of the other ring (e.g., the ceramics ring 114). This "stick and slip" phenomenon may, in turn, generate vibrations within the neck portion 110 of the centrifuge bowl 12.

Figure 3:
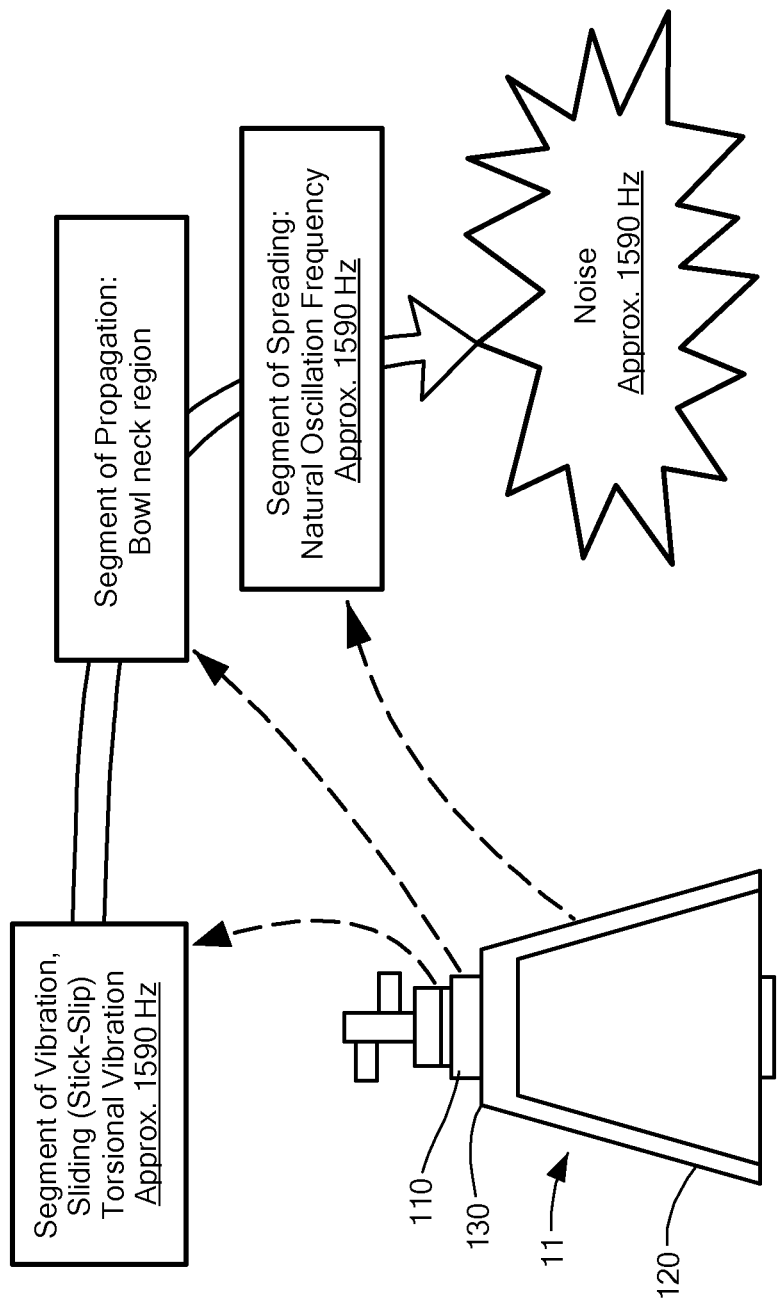
FIG. 3 schematically shows the propagation of vibration through the blood component separation device of FIG. 2 as it rotates, in accordance with embodiments of the present invention.

As shown in FIG. 3, the vibration created by the "stick and slip" phenomenon described above may propagate from the neck portion 110, through the shoulder portion 130, and to the body portion 120. When the vibration reaches the body portion 120, the vibrational and acoustic characteristics of the body portion 120 cause it to emit an audible noise. As one would expect, the audible noise may be disruptive to the subject and operator. Additionally, any vibration may indicate instability within the system, reduce system efficiency, and impact the overall performance of the system.

In order to reduce and/or remove the vibration and audible noise described above, some embodiments of the present invention may include one or more vibration reduction members on the bowl 12. As discussed in greater detail below, these vibration reduction members strengthen and stiffen the neck portion 110 of the bowl 12 which, in turn, reduces the system vibration and reduces/eliminates the noise emitted from the body portion 120.

In one embodiment of the present invention and as shown in FIGS. 4A through 4H, the vibration reduction members may be a plurality of ribs 140 spaced about the bowl 12 and extending between the neck portion 110 and the shoulder 130. The ribs 140 stiffen the neck portion of the bowl 12 and effectively increase the natural vibration frequency of the neck portion 110 without also increasing the natural vibration frequency of the body portion 120.

It is important to note that, by increasing the natural vibration frequency of the neck portion 110 (e.g., by stiffening the neck portion 110 with the ribs 140), the natural frequency of the neck portion 110 is shifted away from the frequency of the vibration created by the sticking and slipping of the sliding surfaces of the rings discussed above. By shifting the natural frequency of the neck portion 110, the amplitude of the vibrations within the neck portion 110 will decrease because there will no longer be resonance (e.g., the vibrations caused by the "stick and slip" phenomenon will no longer be at the natural vibratation/resonance frequency of the neck portion 110).

As mentioned above, the vibrations within the neck portion 110 propagate to the body portion 120 causing the body portion 120 to vibrate and emit an audible noise. However, by reducing the amplitude of the vibrations within the neck portion 110, the vibration propagating to the body portion 120 will similarly be reduced such that it is below the resonance frequency (e.g., the natural vibration frequency) of the body portion 120. By reducing the vibration that is propagated to the body portion 120 (e.g., below the resonance frequency of the body portion 120), the noise emitted by the body portion 120 will be greatly reduced and/or eliminated.

Figure 4E:
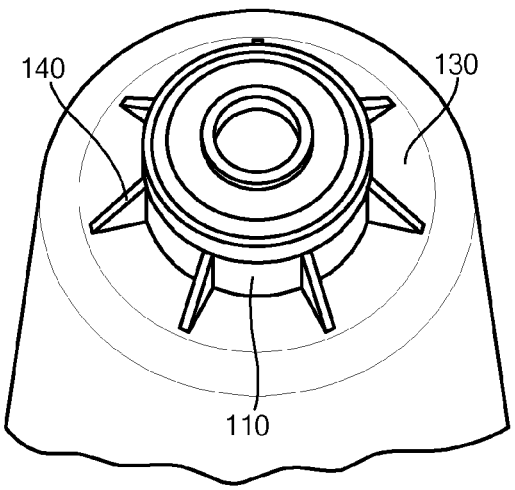
FIGS. 4E through 4H schematically show perspective views of a centrifuge bowl having varying numbers of the vibration reduction members shown in FIG. 4A, in accordance with further embodiments of the present invention.
Figure 4F:
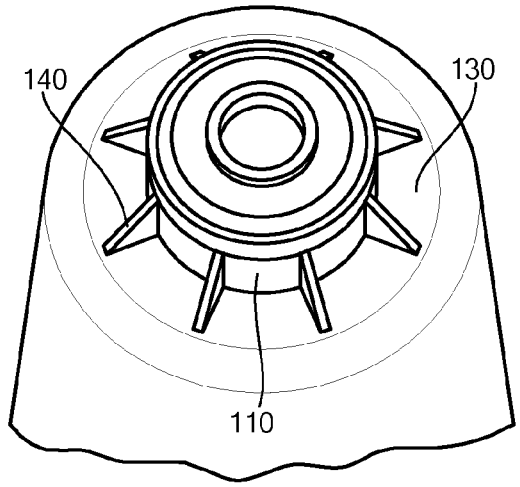
Figure 4G:
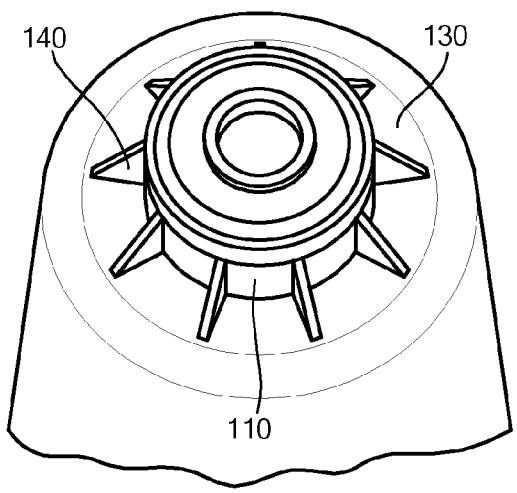
Figure 4H:
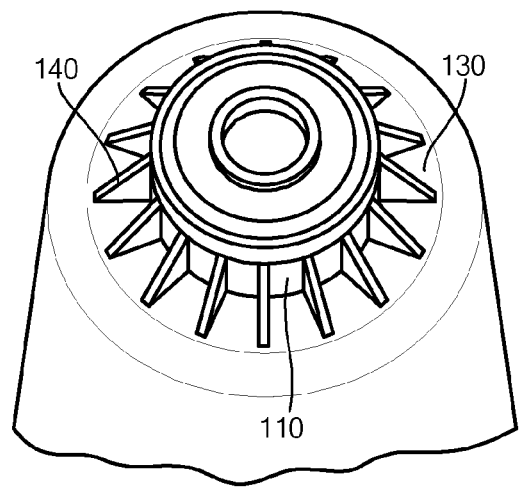

Although FIGS. 4A through 4D show eight, straight ribs spaced about the diameter of the bowl 12 (e.g., on the neck portion 110), as shown in FIGS. 4E-4H, the bowl 12 may include more or less than eight rib members. For example, the bowl may include fewer than eight rib members 140 (e.g., 7 rib members 140 as shown in FIG. 4E) or greater than eight rib members 140 (e.g., 9 rib members 140 shown in FIG. 4G or 16 rib members 140 as shown in FIG. 4H).

Figure 5A:
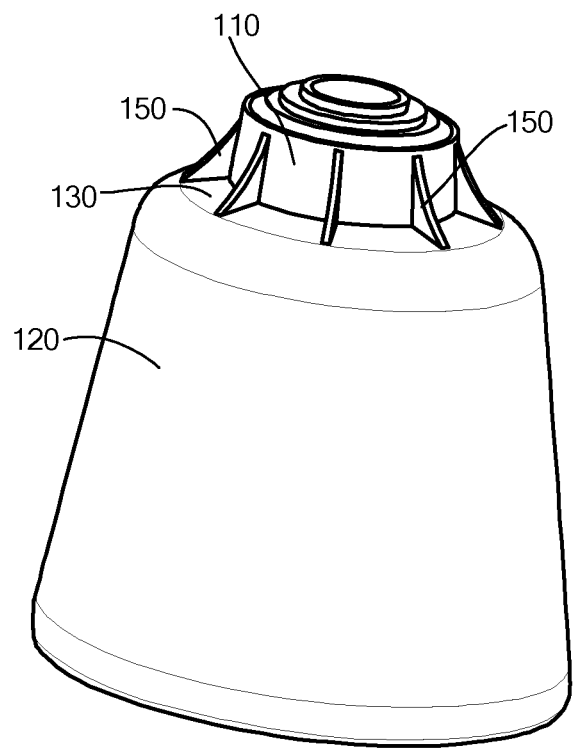
FIG. 5A schematically shows a perspective view of a centrifuge bowl having alternative vibration reduction members, in accordance with embodiments of the present invention.
Figure 5B:
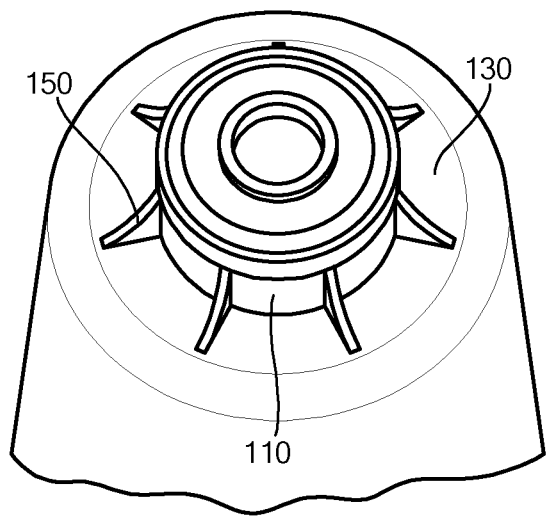
FIGS. 5B through 5F schematically show perspective views of a centrifuge bowl having varying numbers of the alternative vibration reduction members shown in FIG. 5A, in accordance with further embodiments of the present invention.
Figure 5C:
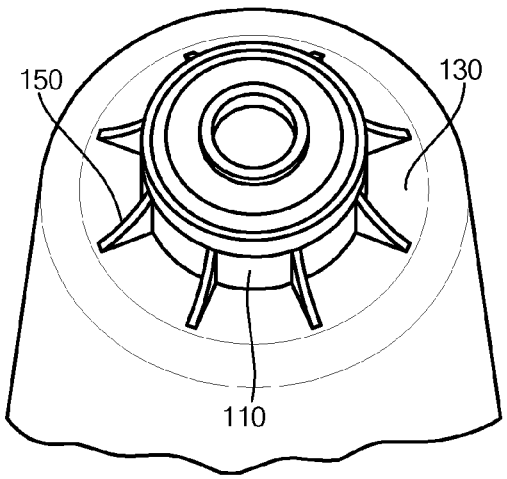
Figure 5D:
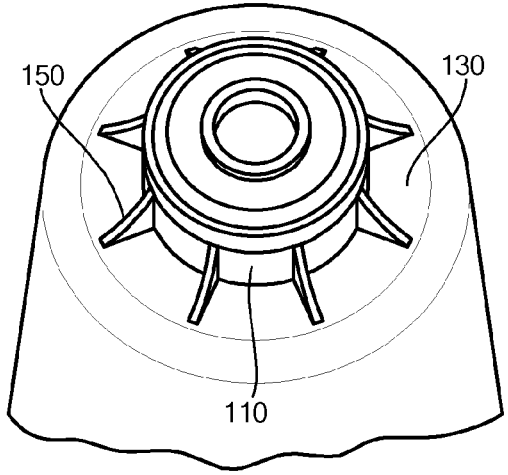
Figure 5E:
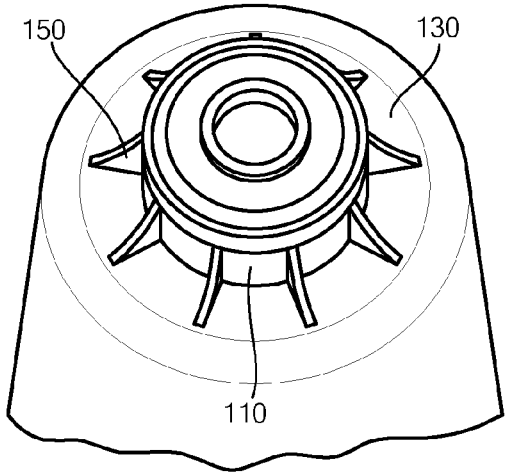
Figure 5F:
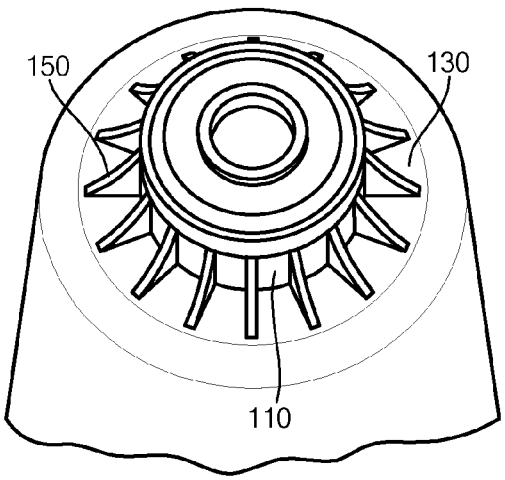

Furthermore, the rib members need not be straight and may have alternative configurations and/or shapes. For example, as shown in FIGS. 5A through 5F, some embodiments of the present invention may include curved rib members 150 spaced about the neck portion 110 and extending from the neck portion 110 to the shoulder portion 130. Like the straight rib members 140, the curved rib members 150 also strengthen and stiffen the neck portion 110 to reduce and/or eliminate the vibration/noise (e.g., by increasing the natural vibration frequency of the neck portion 110). Additionally, also like the straight rib members 140, embodiments having the curved rib members 150 may include any number of the curved ribs 150. For example, the bowl 12 may include 8 rib members 150 (FIGS. 5A, 5C, 5D), less than eight rib members 150 (FIG. 5B) or more than eight rib members 150 (FIGS. 5E and 5F).

Figure 6A:
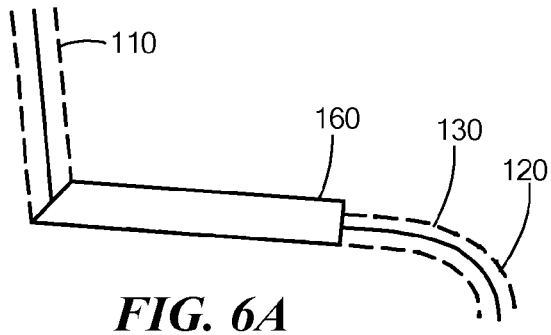
FIGS. 6A through 6D schematically show a portion of a centrifuge bowl having a third type of vibration reduction member, in accordance with additional embodiments of the present invention.
Figure 6B:
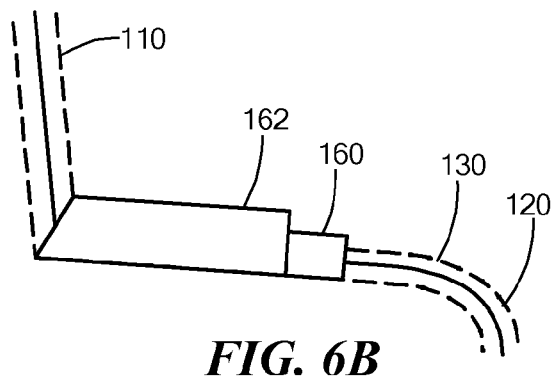
Figure 6C:
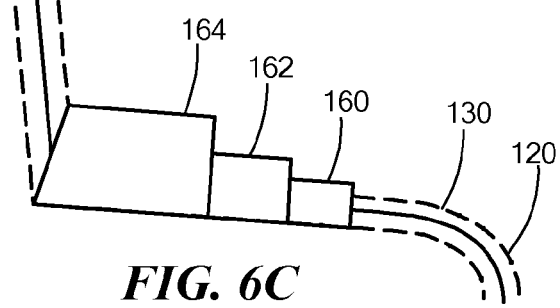
Figure 6D:
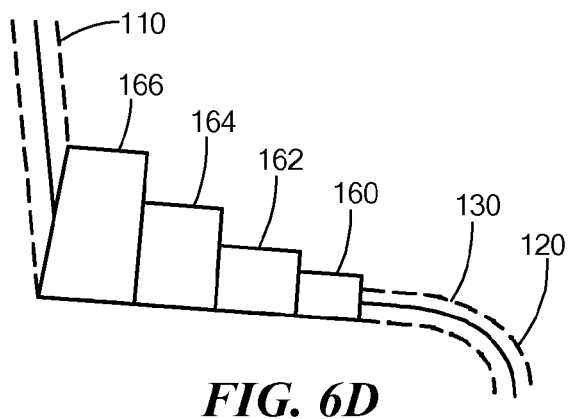

Although the vibration reduction members are discussed above as being ribs (e.g., straight ribs 140 or curved ribs 150), in other embodiments, the vibration reduction members may be areas of increased thickness on the shoulder 130 of the bowl 12, FIGS. 6A-D. For example, the vibration reduction members may be a single area of increased thickness 160 (e.g, as shown in FIG. 6A) or may be an area of increasing thickness. In embodiments having an area of increasing thickness, the thickness may increase gradually or it may increase over one or more steps 160/162/164/166 (e.g., as shown in FIGS. 6B-6D). Like the straight and curved ribs 140/150 discussed above, the thickened areas 160/162/164/166 increase the strength and rigidity of the neck portion 110 to increase the natural vibrational frequency of the neck 110 and decrease/eliminate vibration and/or vibration propagation to the body portion 120.

It is important to note that care must be taken to balance the benefits of the increased strength and rigidity provided by the vibration reduction members (e.g., the ribs 140/150 and/or the thickened area 160) against the additional weight that the vibration reduction members add to the centrifuge bowl 12. In particular, as the weight of the centrifuge bowl 12 increases, the natural vibration frequency of the body portion 120 may change. As the natural vibration frequency of the body portion 120 changes, the vibration/noise reduction benefits of vibration reduction members (e.g., the increased strength and rigidity of the neck portion) may be diminished. For example, if the natural vibrational frequency of the body portion 120 is altered such that it coincides with frequency of the reduced vibrations propagated to the body portion 120 (e.g., the vibrations are at the new resonance frequency of the body portion 120), the body portion 120 may then still vibrate significantly and emit an audible noise. Therefore, the thickness of the ribs members 140/150 and the thickened areas 160 on the neck portion 110 must be such that they do not increase the weight of the centrifuge device enough to significantly alter/increase the natural vibrational frequency of the body portion 120.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A centrifuge bowl for separating whole blood into blood components comprising:
   a rotatable body having a body portion and a neck portion, the body portion defining an interior for receiving whole blood, the body being rotatable to separate the whole blood into a plurality of blood components, the body portion also having a shoulder portion extending between the body portion and the neck portion, the body portion, the neck portion and the shoulder portion being integral;
   an inlet in fluid communication with the interior of the rotatable body, the inlet configured to introduce the whole blood into the rotatable body; and
   at least one vibration reduction member located on the shoulder portion and configured to stiffen at least a portion of the rotatable body and reduce vibration of the centrifuge bowl as the bowl is rotated.

2. A centrifuge bowl according to claim 1 wherein the at least one vibration reduction member includes a plurality of rib members.

3. A centrifuge bowl according to claim 2, wherein the rib members are curved.

4. A centrifuge bowl according to claim 2, wherein the rib members are straight.

5. A centrifuge bowl according to claim 1, wherein the at least one vibration reduction member includes a thickened area located on the shoulder portion.

6. A centrifuge bowl according to claim 5, wherein the thickened area increases in thickness towards an axis of rotation of the bowl.

7. A centrifuge bowl according to claim 6, wherein the increase in thickness is stepped.

8. A centrifuge bowl according to claim 1, wherein the rotatable body is frustoconical.

9. A centrifuge bowl according to claim 1, wherein the at least one vibration reduction member is configured to increase the natural vibration frequency of a first portion of the centrifuge bowl without increasing the natural vibration frequency of a second portion of the centrifuge bowl, thereby reducing the vibration of the centrifuge bowl as the bowl is rotated.

10. A centrifuge bowl according to claim 9, wherein the first portion of the centrifuge bowl is the neck portion and the second portion is the body portion.

11. A centrifuge bowl according to claim 2, wherein each of the plurality of rib members extend radially outward from the neck portion.

12. A centrifuge bowl according to claim 2, wherein the plurality of rib members are equally spaced about the neck portion.

13. A centrifuge bowl according to claim 2, wherein each of the plurality of rib members extend from the neck portion to the shoulder portion.

14. A centrifuge bowl according to claim 2, wherein each of the plurality of rib members reduce in height with increasing distance from the axis of rotation.

15. A centrifuge bowl according to claim 2, wherein each of the plurality of rib members have a longitudinal axis that is perpendicular to and intersects the axis of rotation of the rotatable body.

16. A centrifuge bowl according to claim 7, wherein the thickened area has a plurality of steps.

17. A centrifuge bowl according to claim 1 further comprising an outlet, the outlet in fluid communication with the interior of the bowl and configured to remove one or more of the blood components from the centrifuge bowl.

18. A centrifuge bowl according to claim 1 further comprising a rotary seal attached to the rotatable body, the rotary seal fluidly coupling the inlet to the body portion.

19. A centrifuge bowl according to claim 18, wherein the rotary seal includes a first ring and a second ring.

20. A centrifuge bowl according to claim 1 further comprising a core, the core being coaxial with the interior and creating a whole blood separation region between an outer wall of the core and an inner wall of the rotatable body.

* * * * *